United States Patent
Yamamoto et al.

(10) Patent No.: US 7,211,636 B2
(45) Date of Patent: May 1, 2007

(54) IONIC COMPOUND, RESIN COMPOSITION CONTAINING THE SAME AND USE THEREOF

(75) Inventors: Yugo Yamamoto, Sodegaura (JP); Yasushi Mizuta, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 11/157,972

(22) Filed: Jun. 22, 2005

(65) Prior Publication Data

US 2006/0293477 A1    Dec. 28, 2006

(30) Foreign Application Priority Data

Jun. 22, 2004    (JP)    ............................. 2004-183537

(51) Int. Cl.
*C08F 216/14*    (2006.01)
(52) U.S. Cl. ...................... 526/307.5; 526/312; 568/1; 568/6; 568/77; 556/7
(58) Field of Classification Search ................ 526/348, 526/312, 307.5; 568/6, 1, 77; 556/7
See application file for complete search history.

(56) References Cited

U.S. PATENT DOCUMENTS 5,468,902 A * 11/1995 Castellanos et al. ............ 568/6
6,368,769 B1 * 4/2002 Ohkawa et al. .......... 430/270.1

FOREIGN PATENT DOCUMENTS

| EP | 1 591 098 A1 | 11/2005 |
|----|---|---|
| JP | 2557782 B2 | 7/1994 |
| JP | A-09-278814 | 10/1997 |
| JP | 2000-186071 A | 7/2000 |
| JP | A-2004-027073 | 1/2004 |
| JP | 2004-139070 | 5/2004 |
| JP | A-2005-187636 | 7/2005 |
| WO | WO 03/106582 A1 | 12/2003 |
| WO | WO 2004/031197 A1 | 4/2004 |

OTHER PUBLICATIONS

Partial European Search Report issued Aug. 29, 2006 in corresponding EP Application 05013236.4-2117.
Toba, Yasumasa, "Design of Photoinitiator System with Onion Borates for Polymerization", *Chemical Business HQ's, Color Material R and D Division*, Toyo Ink Manufacturing Co., Ltd., Tsukuba, Ibaraki, Japan (2002) 59(8) 449-459 pp. 9-17 (XP-002387673).

* cited by examiner

*Primary Examiner*—Ling-Sui Choi
(74) *Attorney, Agent, or Firm*—Buchanan, Ingersoll & Rooney, PC

(57) ABSTRACT

An ionic compound comprising a cationic portion having a hydroxyl group and/or a carboxylic acid group and an anionic portion of the formula (1):

$$[BR_4]^- \qquad (1)$$

wherein R may be the same or different and represents a phenyl group substituted with F or $CF_3$. Preferably, the anionic portion is $[B(C_6F_5)_4]^-$, $[B(C_6H_4CF_3)_4]^-$ or $[B(C_6H_3F_2)_4]^-$. In other aspects, a radiation polymerization initiator and a resin composition comprising the ionic compound are provided. A resin composition prepared by using the radiation polymerization initiator generates a small amount of outgas during reaction and has excellent reactivity and transparency.

6 Claims, No Drawings

IONIC COMPOUND, RESIN COMPOSITION CONTAINING THE SAME AND USE THEREOF

BACKGROUND OF THE INVENTION

1. Field of the Invention

The present invention relates to an ionic compound, and a radiation polymerization initiator comprising the compound, a resin composition containing the initiator and the use thereof.

2. Description of the Related Art

An onium salt or an organometallic complex salt is known as a photocationic polymerization initiator of a monomer and/or a polymer containing a functional group such as epoxy, vinyl ether, and oxetane. It has been confirmed that these salts exhibit an excellent hardening ability when an anion of an initiator salt is $SbF_6^-$. However, there is a risk of toxicity from the initiator salt containing this type of anion. Patent Document 1 discloses that tetrakis(pentafluorophenyl)borate, which is an anion having nucleophilicity similar to that of $SbF_6^-$, is used in a new onium borate or borate of an organometallic complex used as the photocationic polymerization initiator. Patent Document 2 discloses a new aromatic sulfonium compound, a photo-acid generator comprising the compound and a photopolymerizable composition containing the generator. However, there are problems in regards to the environment and pollution to peripheral members caused by outgas generated from the onium salt, the onium salt being used as a countercation during polymerization or crosslinking reactions by a photochemical means or under electron beam irradiation.

[Patent Document 1] Japanese Patent No. 2557782
[Patent Document 2] Japanese Patent Laid-Open No. 2000-186071

SUMMARY OF THE INVENTION

Accordingly, it is an object of the present invention to provide a resin composition prepared by using a new radiation polymerization initiator that generates a small amount of outgas during reaction and has excellent reactivity and transparency.

The present inventors diligently repeated studies in order to develop a new useful radiation polymerization initiator. As a result, the inventors found a new radiation polymerization initiator that generates a small amount of outgas during the reaction and has excellent reactivity and transparency by finding a new ionic compound in the initiator and using a new cationic portion.

Specifically, an ionic compound comprises a cationic portion having a hydroxyl group and/or a carboxylic acid group and an anionic portion of the formula (1):

$$[BR_4]^- \quad (1)$$

wherein R may be the same or different and represents a phenyl group substituted with F or $CF_3$.

In addition, it is preferable that the ionic compound has the anionic portion of $[B(C_6F_5)_4]^-$, $[B(C_6H_4CF_3)_4]^-$ or $[B(C_6H_3F_2)_4]^-$, and the cationic portion of $[HO(CH_2)_n\text{—}O\text{-}\Phi]_2\text{-}S^+\text{-}\Phi\text{-}S\text{-}\Phi\text{-}S^+\text{-}[\Phi\text{-}O\text{—}(CH_2)_nOH]_2$, $[HOOC(CH_2)_2\text{—}O\text{-}\Phi]_2\text{-}S^+\text{-}\Phi\text{-}S\text{-}\Phi\text{-}S^+\text{-}[\Phi\text{-}O\text{—}(CH_2)_2COOH]_2$, $[HO(CH_2)_n\text{—}O\text{-}\Phi]_2\text{-}S^+\text{-}\Phi\text{-}S\text{-}\Phi$, $[HOOC(CH_2)_n\text{—}O\text{-}\Phi]_2\text{-}S^+\text{-}\Phi\text{-}S\text{-}\Phi$, $[HO(CH_2)_n\text{—}O\text{-}\Phi]_2\text{-}S^+\text{-}\Phi$, $[HO(CH_2)_n\text{—}O\text{-}\Phi]\text{-}S^+\text{-}\Phi_2$, $[HOOC(CH_2)_n\text{—}O\text{-}\Phi]_2\text{-}S^+\text{-}\Phi$, $[HOOC(CH_2)_n\text{—}O\text{-}\Phi]\text{-}S^+\text{-}\Phi_2$, $HO(CH_2)_n\text{—}O\text{-}\Phi\text{-}I^+\text{-}\Phi$, $HOOC(CH_2)_n\text{—}O\text{-}\Phi\text{-}I^+\text{-}\Phi$, $[HO(CH_2)_n\text{—}O\text{-}\Phi]_2I^+$ or $[HOOC(CH_2)_n\text{—}O\text{-}\Phi]_2I^+$. In a method for preparation of the above-described ionic compound, the ionic compound is prepared by an exchange reaction of a salt of the cationic portion with an alkali metal salt of the anionic portion. In addition, the radiation polymerization initiator comprises the above-described ionic compound, and the resin composition contains the radiation polymerization initiator. Moreover, an adhesive or a coating agent contains the above-described resin composition.

DESCRIPTION OF THE PREFERRED EMBODIMENTS

Hereinafter, the invention will be described in detail.

<Ionic Compound>

The ionic compound of the invention has the cationic portion having the hydroxyl group and/or the carboxylic acid group and the anionic portion represented by the formula (1):

$$[BR_4]^- \quad (1)$$

wherein R may be the same or different and represents a phenyl group substituted with F or $CF_3$.

Cationic Portion

The cationic portion has the hydroxyl group and/or the carboxylic acid group. In addition, the cationic portion is preferably represented by the formula (2):

$$[(A)_k(A^+)_1(R^1)_m(R^2)_n]^+ \quad (2)$$

wherein A may be used alone or in combination of two or more selected from I, S, Se, N, Fe, Mn, Cr, Co, Mo, W and Re; $R^1$ is a phenyl group; $R^2$ is selected from the combination of an aromatic ring, a heterocyclic ring, an alicyclic ring, an alkyl group and an alkoxy group, each of which has 6 to 32 carbon atoms and has a hydroxyl group and/or a carboxylic acid group; k is an integer of 0 to 4; 1 is an integer of 1 to 4; m is an integer of 0 to 4; and n is an integer of 2 to 6. $A^+$ and A are bonded by $R^1$ and A is preferably I or S.

In addition, the cationic portion is preferably $[HO(CH_2)_n\text{—}O\text{-}\Phi]_2\text{-}S^+\text{-}\Phi\text{-}S\text{-}\Phi\text{-}S^+\text{-}[\Phi\text{-}O\text{—}(CH_2)_nOH]_2$, $[HOOC(CH_2)_2\text{—}O\text{-}\Phi]_2\text{-}S^+\text{-}\Phi\text{-}S\text{-}\Phi\text{-}S^+\text{-}[\Phi\text{-}O\text{—}(CH_2)_2COOH]_2$, $[HO(CH_2)_n\text{—}O\text{-}\Phi]_2\text{-}S^+\text{-}\Phi\text{-}S\text{-}\Phi$, $[HOOC(CH_2)_n\text{—}O\text{-}\Phi]_2\text{-}S^+\text{-}\Phi\text{-}S\text{-}\Phi$, $[HO(CH_2)_n\text{—}O\text{-}\Phi]_2\text{-}S^+\text{-}\Phi$, $[HO(CH_2)_n\text{—}O\text{-}\Phi]\text{-}S^+\text{-}\Phi_2$, $[HOOC(CH_2)_n\text{—}O\text{-}\Phi]_2\text{-}S^+\text{-}\Phi$, $[HOOC(CH_2)_n\text{—}O\text{-}\Phi]\text{-}S^+\text{-}\Phi_2$, $HO(CH_2)_n\text{—}O\text{-}\Phi\text{-}I^+\text{-}\Phi$, $HOOC(CH_2)_n\text{—}O\text{-}\Phi\text{-}I^+\text{-}\Phi$, $[HO(CH_2)_n\text{—}O\text{-}\Phi]_2I^+$ or $[HOOC(CH_2)_n\text{—}O\text{-}\Phi]_2I^+$.

Anionic Portion

The anionic portion is $[BR_4]^-$ wherein R may be the same or different and represents a phenyl group substituted with F or $CF_3$.

In view of reactivity, the anionic portion is preferably $[B(C_6F_5)_4]^-$, $[B(C_6H_4CF_3)_4]^-$ or $[B(C_6H_3F_2)_4]^-$, and more preferably $[B(C_6F_5)_4]^-$.

<Method for Preparation of Ionic Compound>

According to the method for preparation of the ionic compound, the ionic compound can be prepared by an exchange reaction of a salt (a halide such as a chloride and a iodide, hexafluorophosphate, tetrafluoroborate, tosylate, or the like) of the cationic portion with an alkali metal salt (sodium, lithium, or potassium salt) of the anionic portion. The desired ionic compound can be recovered by filtration when it is precipitated in the solid form or by extraction with a suitable solvent when it is in the oil form.

The alkali metal salt of the anionic portion, according to the known method, may be prepared by the exchange reaction of a haloborate compound with the desired organometallic compound (compounds of magnesium, lithium, tin, or the like) having a hydrocarbon group in the respective stoichiometric amounts and, if necessary, followed by hydrolysis with an aqueous alkali metal halide solution. This synthesis is described in, for example, "Journal of Organometallic Chemistry", Vol. 178, pp. 1–4, 1979.

<Radiation Polymerization Initiator>

The radiation polymerization initiator of the invention comprises the ionic compound of the invention. The term "radiation" as used herein means an electromagnetic ray or a corpuscular ray, and preferably, an ultraviolet ray having a wavelength of 400 nm or less, a visible ray having a wavelength of 400 nm to 800 nm, and an infrared ray having a wavelength of 800 nm or more. Types of the radiation to be used may be appropriately selected depending on uses of the resin composition in which the radiation polymerization initiator is blend. The radiation polymerization initiator of the invention can be used in polymerization or crosslinking of a monomer and/or a polymer having a functional group such as epoxy, oxetane, and vinyl ether. Moreover, a borate of the organometallic complex can be used as a thermal polymerization initiator.

<Resin Composition>

The resin composition of the invention comprises a monomer and/or a polymer having a functional group which is photocationically polymerizable, such as epoxy, oxetane, and vinyl ether and the radiation polymerization initiator of the invention. In addition, it is also possible to add a coupling material such as a silane coupling agent and a titanate-based coupling agent, an inorganic filler such as calcium carbonate, silica, and talc and an organic filler, a leveling agent for providing surface smoothness, and a polymeric material such as a polymer epoxy resin for providing coating performance, an acrylic polymer and a polyester resin.

<Adhesive and Coating Agent>

The adhesive and the coating agent of the invention comprise the above-described resin composition. The adhesive and the coating agent are used to adhere or coat an inorganic compound such as a glass and a metal and an organic compound such as plastics, and compounds obtained by conducting a surface treatment on the surfaces thereof or forming a thin film thereon. More specifically, the adhesive and the coating agent can be used as those for a liquid crystal display and an electronic display such as an organic EL and an electronic paper; an electronic material such as a resist for a CCD package or a printed circuit board and a photosensitive resin for printing; an adhesive for bonding an optical disk such as CD and DVD or a surface coating agent thereof; automobile painting; surface coats for coating the surface of a vessel such as a can and a bottle; coating the surface of optical lens and fixing thereof; optical application such as optical fiber connection and prism bonding; three-dimensional composition; other surface treating materials such as a coating material, a surface reforming material, an adhesive, and a mold releasing agent; and patterning such as offset printing and relief printing, gravure printing, silk-screen printing and jet printing. However, it is not limited to the above-mentioned applications when a radiation curable adhesive or coating agent is used.

EXAMPLES

Hereinafter, the invention will be explained in more detail with reference to the following Examples, but it is in no way intended to limit the scope of the invention.

Synthesis Example 1

Synthesis Method of bis(4-(di(4-(2-hydroxyethyl) phenylsulfonio)-phenyl)sulfide [HO(CH$_2$)$_2$— 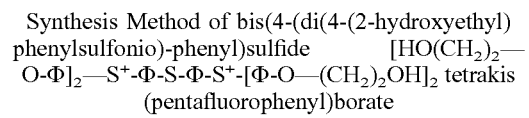 tetrakis (pentafluorophenyl)borate Into a 1000-ml four-necked round bottomed flask previously dried under an argon atmosphere and equipped with a mechanical stirrer, a water cooling type reflux condenser, a thermometer and a dropping funnel were introduced 31.71 g (0.33 mol) of meta-sulfone and 3.41 g (0.024 mol) of phosphorus pentoxide, and the reaction mixture was heated at 70° C. and stirred for 3 hours. The resultant homogeneous solution was cooled to room temperature. To the resulting solution were added 26.3 g (0.033 mol) of 4,4'-bishydroxy-ethoxyphenylsulfide and 3.07 g (0.0165 mol) of diphenyl sulfide and the reaction mixture was stirred at room temperature for 5 hours.

To the reaction mixture was gradually added dropwise with stirring 380 ml (0.0333 mol) of an aqueous 3% sodium tetrakis(pentafluorophenyl)borate solution (manufactured by Nippon Shokubai Co., Ltd.) and the resulting mixture was stirred at room temperature for 3 hours. The precipitated solid was separated by filtration, dried, and then heated (70° C.) and dissolved in isopropanol. Next, the resultant was separated by filtration and dried to obtain 15.79 g (0.011 mol) of a white solid.

Example 1

0.3 g of bis(4-(di(4-(2-hydroxyethyl)phenylsulfonio)-phenyl)sulfide tetrakis(pentafluorophenyl)borate synthesized in Synthesis Example 1 was dissolved in a mixed solution of 8 g of bisphenol A diglycidyl ether (R-140 manufactured by Mitsui Chemicals, Inc.) and 2 g of 3-ethyl-3-hydroxymethyloxetane (EOXA manufactured by Toagosei Co., Ltd.) at 60° C. to prepare a resin solution.

1. Curability Evaluation

The resin solution was continuously irradiated with light intensity of 20 mW/cm$^2$ from an ultraviolet lamp (Lightingcure LC6 manufactured by Hamamatsu Photonics K.K.) to measure the time the solution became tack-free to the touch. The result was shown in Table 1.

2. Measurement of Outgas Amount 1 g of the resin solution was weighed in a 20 mL vial. The vial was sealed with a stopper and then irradiated with an ultraviolet ray of 10 J/cm$^2$ from an ultraviolet lamp (Lightingcure LC6 manufactured by Hamamatsu Photonics K.K.). The vial was heated at 80° C. for 1 hour and returned to room temperature. The amount of outgas generated in the gaseous phase portion thereof was measured by gas chromatography. The result was shown in Table 1.

3. Evaluation of Transparency

The resin solution was applied onto a glass plate using an applicator so as to have a thickness of 100 μm. The resin solution was irradiated with an ultraviolet ray of 10 J/cm$^2$ from the above-mentioned ultraviolet lamp and then the cured film was peeled off from the glass plate. The light transmittance at wavelength of 400 nm of the film was measured using a MultiSpec-1500 (manufactured by Shimadzu Corporation).

4. Evaluation of Adhesive Strength

A glass plates was combined with another glass plate through the resin composition (a thickness of 20 μm) interposed therebetween and they were irradiated with an ultraviolet ray of 10 J/cm$^2$ from the above-mentioned ultralamp to cure and adhere them. When these two plates were separated therefrom, the adhesive strength thereof was measured at a tension rate of 2 mm/min.

[Comparative Example 1]

Diphenyliodonium tetrakis(pentafluorophenyl)borate (RHODORSIL Photoinitiator 2074 manufactured by Rhodia, Inc.) was used as a photoinitiator to prepare a resin solution with the same blending proportions as in Example. The hardening ability and the amount of outgas of the resin solution were measured. The results were shown in Table 1.

Comparative Example 2

Diphenyliodonium hexafluorophosphate (Irgacure 250 manufactured by Ciba Specialty Chemicals Holding Inc.) was used as the photoinitiator to prepare a resin solution with the same blending proportions as in Example. The hardening ability and the amount of outgas of the resin solution were measured. The results were shown in Table 1.

TABLE 1

|  | Example 1 | Comparative Example 1 | Comparative Example 2 |
|---|---|---|---|
| Hardening ability Tack-free time (sec) | 40 | 37 | 64 |
| Amount of outgas (μg) | 40 | 110 | 105 |
| Light transmittance (%) | 95 | 65 | 93 |
| Adhesive strength (MPa) | 17 | 12 | 16 |

According to the invention, it is possible to obtain a new radiation polymerization initiator that generates a small amount of outgas during reaction and has excellent reactivity and transparency.

The radiation polymerization initiator of the invention generates a small amount of outgas during reaction and has excellent reactivity and transparency, and thus is useful in a resin composition capable of polymerizing or crosslinking a monomer and/or a polymer containing an organic functional group used as electrical and electronic materials, under radiation.

What is claimed is:

1. An ionic compound comprising a cationic portion and an anionic portion, wherein the cationic portion is $[HO(CH_2)_n-O-\Phi]_2-S^+-\Phi-S-\Phi-S^+-[\Phi-O-(CH_2)_nOH]_2$, $[HOOC(CH_2)_2-O-\Phi]_2-S^+-\Phi-S-\Phi-S^+-[\Phi-O-(CH_2)_2COOH]_2$, $[HO(CH_2)_n-O-\Phi]_2-S^+-\Phi-S-\Phi$, $[HOOC(CH_2)_n-O-\Phi]_2-S^+-\Phi-S-\Phi$, $[HO(CH_2)_n-O-\Phi]_2-S^+-\Phi$, $[HO(CH_2)_n-O-\Phi]-S^+-\Phi_2$, $[HOOC(CH_2)_n-O-\Phi]_2-S^+-\Phi$, $[HOOC(CH_2)_n-O-\Phi]-S^+-\Phi_2$, $HO(CH_2)_n-O-\Phi-I^+-\Phi$, $HOOC(CH_2)_n-O-\Phi-I^+-\Phi$, $[HO(CH_2)_n-O-\Phi]_2I^+$ or $[HOOC(CH_2)_n-O-\Phi]_2I^+$ and the anionic portion is represented by the formula (1):

$$[BR_4]^- \qquad (1)$$

wherein R may be the same or different and represents a phenyl group substituted with F or $CF_3$, and n is an integer of 2 to 6.

2. The ionic compound according to claim 1, wherein the anionic portion is $[B(C_6F_5)_4]^-$, $[B(C_6H_4CF_3)_4]^-$, or $[B(C_6H_3F_2)_4]^-$.

3. A radiation polymerization initiator comprising the ionic compound according to claim 1.

4. A resin composition comprising the radiation polymerization initiator according to claim 3 and monomer containing a functional group which is photocationically polymerizable.

5. An adhesive or a coating agent containing the resin composition according to claim 4.

6. A method for preparation of an ionic compound, wherein the ionic compound according to claim 1 is prepared by an exchange reaction of a salt of the cationic portion with an alkali metal salt of the anionic portion.

* * * * *